United States Patent [19]

Patel

[11] 4,162,673

[45] Jul. 31, 1979

[54] METHOD OF TESTING THE POSITION OF A NEEDLE ASSEMBLY IN THE EPIDURAL SPACE

[75] Inventor: Bhupendra C. Patel, Elgin, Ill.

[73] Assignee: The Kendall Company, Boston, Mass.

[21] Appl. No.: 889,478

[22] Filed: Mar. 23, 1978

Related U.S. Application Data

[62] Division of Ser. No. 680,959, Apr. 28, 1976, abandoned.

[51] Int. Cl.$^2$ .............................................. A61B 5/00
[52] U.S. Cl. .................................... 128/748; 128/216
[58] Field of Search ................. 128/2 B, 2 R, 2.05 D, 128/2.05 E; 73/200, 215, 230; 116/70, 114 C, 114 AJ, 114 PV, 117 C, 118 R

[56] References Cited

U.S. PATENT DOCUMENTS 3,874,369   4/1975   Pannier, Jr. et al. ....... 128/2.05 E X

*Primary Examiner*—William E. Kamm
*Attorney, Agent, or Firm*—Powell L. Sprunger

[57] ABSTRACT

A method of testing the position of a needle assembly in the epidural space of a patient's body, the needle assembly having a tip and an elongated passageway communicating between the tip and a shallow open cavity, comprising the steps of positioning the tip and a distal passageway portion of the assembly inside the patient's body with the tip located adjacent the epidural space and with the cavity located outside the patient's body in an upright position, placing a testing liquid in the upright cavity of the assembly, and advancing the assembly into the body while determining whether the testing liquid passes from the cavity to the passageway or the exterior of the needle assembly to ascertain the position of the needle assembly tip in the patient's body.

3 Claims, 9 Drawing Figures

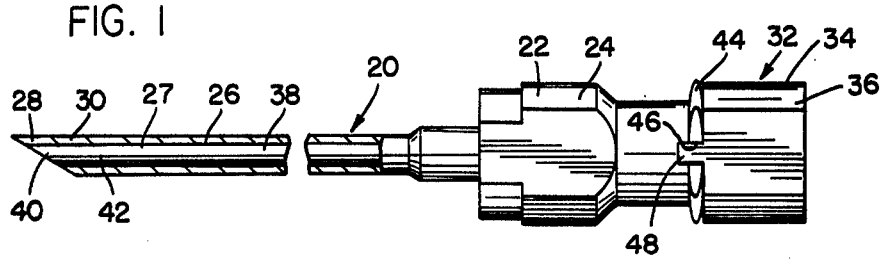
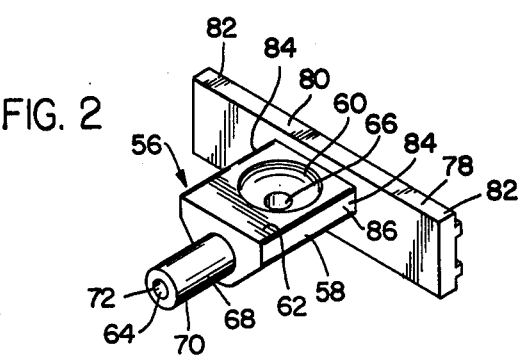
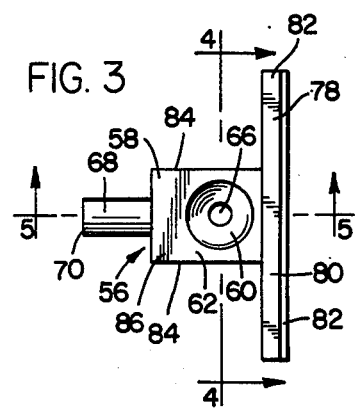
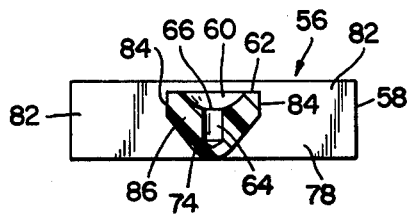
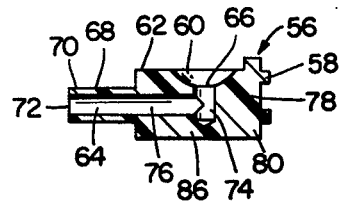
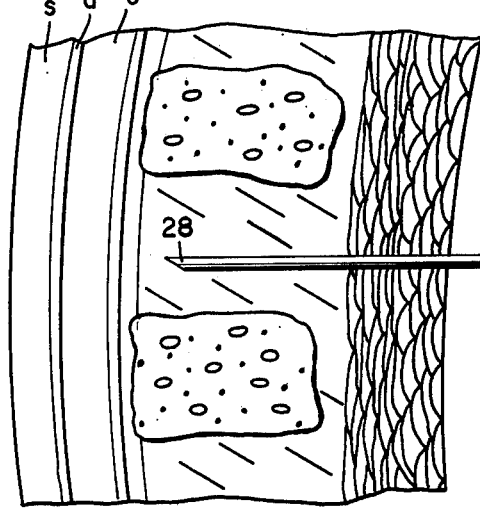

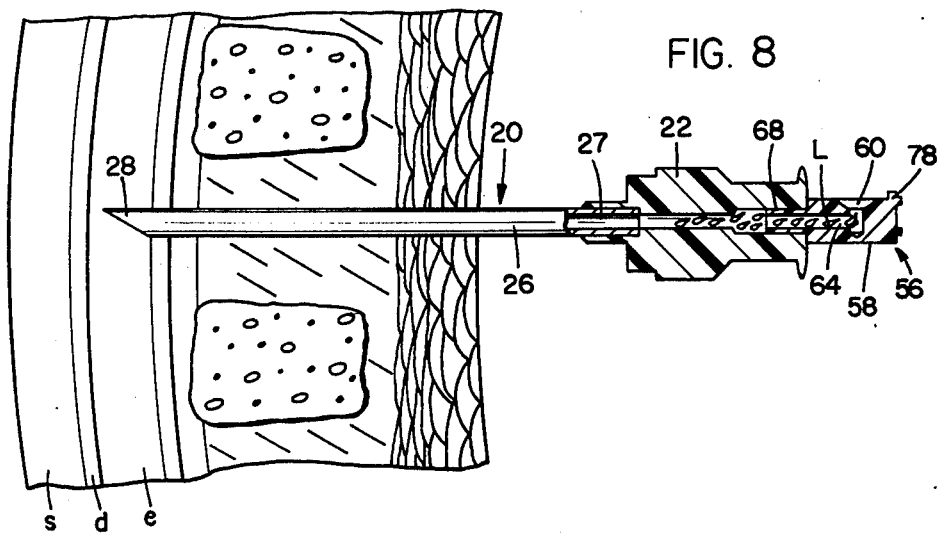
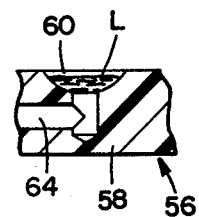
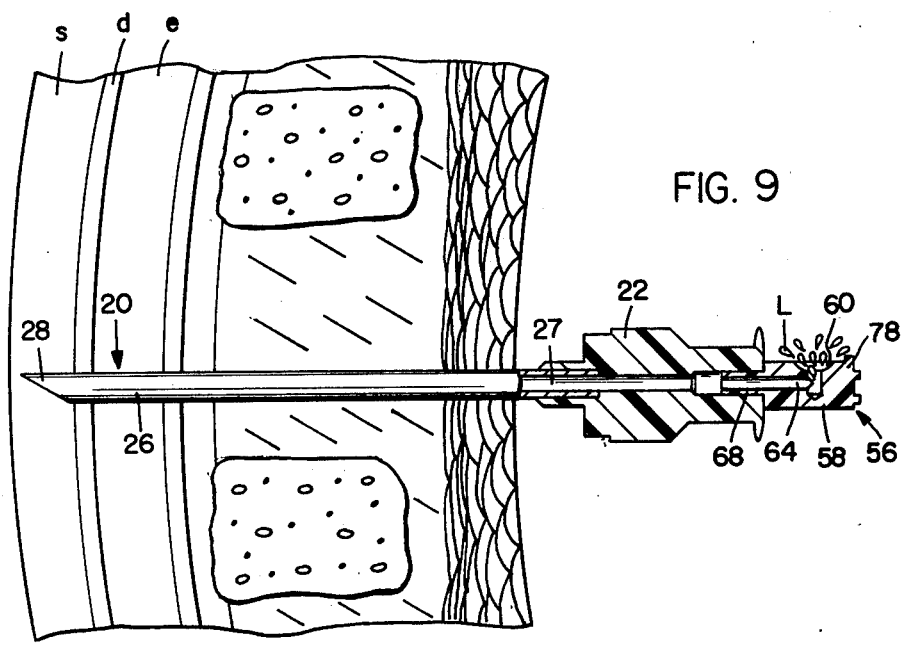

METHOD OF TESTING THE POSITION OF A NEEDLE ASSEMBLY IN THE EPIDURAL SPACE

This is a division of application Ser. No. 680,959 filed Apr. 28, 1976, now abandoned.

BACKGROUND OF THE INVENTION

The present invention relates to position testing devices for a patient's body.

During certain medical procedures, such as an epidural anesthesia procedure, it is necessary to position the tip of a needle at a relatively precise position inside the patient's body. During this particular procedure, the needle tip should be located in the potential epidural space where the body pressure is normally slightly negative, and never positive. If the needle tip has been advanced too far into the body, it projects through the dura mater into the subarachnoid space where the body pressure is positive.

Epidural anesthesia has become popular among anesthesiologists and surgeons since it does not entail the risks associated with general anesthesia, and does not require that the dura mater be punctured. However, locating the epidural space can be relatively difficult since it is a potential space, i.e., an interface between two tissues which are normally held together by a slight negative pressure. Prior testing methods for the epidural space involve the use of tactile sense with syringes or a drop of liquid placed in the needle hub. The syringe tests have not been satisfactory since they rely on subjective judgment of the user under his control. The hub or Guiteras test also has not been suitable since the liquid drop frequently falls out of the hub, and thus may result in a false indication of the needle location.

SUMMARY OF THE INVENTION

A principal feature of the present invention is the provision of a method of testing the position of a needle assembly in the epidural space of a patient's body.

The needle assembly used in the applicant's method has a tip and an elongated passageway communicating between the tip and a shallow open cavity. The tip and a distal passageway portion of the assembly are positioned inside the patient's body with the tip located adjacent the epidural space and with the cavity located outside the patient's body in an upright position. A testing liquid is placed in the upright cavity of the assembly, and the assembly is advanced into the body.

A feature of the invention is that the user may ascertain the position of the assembly tip relative to the epidural space by determining whether the liquid passes from the cavity into the passageway or the exterior of the needle assembly.

Another feature of the invention is that the advancement of the assembly is stopped if the liquid passes from the cavity into the passageway since the tip is located in the epidural space.

Yet another feature of the invention is that the assembly is slightly withdrawn and the procedure is partially repeated if the liquid passes from the cavity to the exterior of the assembly, since the tip has passed through the dura mater into the subarachnoid space.

Further features will become more fully apparent in the following description of the embodiments of this invention and from the appended claims.

DESCRIPTION OF THE DRAWINGS

In the drawings:

FIG. 1 is a fragmentary elevational view, taken partly in section, of a spinal needle and stylet;

FIG. 2 is a perspective view of a position testing device of the present invention;

FIG. 3 is a top plan view of the testing device of FIG. 2;

FIG. 4 is a sectional view taken substantially as indicated along the line 4—4 of FIG. 3;

FIG. 5 is a sectional view taken substantially as indicated along the line 5—5 of FIG. 3;

FIG. 6 is a diagrammatic sectional view of a patient's body showing the needle and stylet of FIG. 1 as positioned in the patient;

FIG. 7 is a fragmentary sectional view of the testing device of FIG. 2 illustrating a testing liquid as placed in a cavity of the device;

FIG. 8 is a diagrammatic sectional view of the patient's body showing the needle tip as positioned in the epidural space of the patient; and FIG. 9 is a diagrammatic sectional view of the patient's body showing the needle tip as positioned in the subarachnoid space of the patient.

DESCRIPTION OF THE PREFERRED EMBODIMENTS

Referring now to FIG. 1, there is shown a hollow spinal needle generally designated 20 having a hub 22 adjacent a proximal end 24 of the needle, a hollow shaft 26 secured to the hub 22, a lumen 27, and a bevel tip 28 adjacent a distal end 30 of the needle 20. As shown, a stylet generally designated 32 is removably received in the needle 20. The stylet 32 has an end member 34 adjacent a proximal end 36 of the stylet 32, a solid shaft 38 connected to the member 34 and received in the hollow shaft 26 of the needle 20, with the shaft 38 having a bevel tip 40 adjacent a distal end 42 of the stylet 32 forming a continuous distal end surface between the needle tip 28 and stylet tip 40 when the stylet 32 is properly positioned within the needle 20. The needle hub 22 has an outwardly directed flange 44 at its proximal end, and the flange 44 has a reference notch 46 to receive a reference protuberance 48 extending distally of the stylet member 34. Accordingly, the stylet 32 may be rotated within the needle 20 until the protuberance 48 is located in the notch 46, as shown, such that the flange 44 and member 34 mate together and position the stylet tip 40 at its proper location relative the needle tip 28.

With reference to FIG. 6, at the start of an epidural anesthesia procedure, a patient may be positioned on his side and the needle 20 and internal stylet 32 are inserted by the physician into the patient's back until needle and stylet tips are located somewhat near the epidural space e of the patient. During this time, the stylet 32 prevents coring of body tissue by the needle 20. After the needle 20 has been properly positioned in the patient, the stylet 32 is removed from the needle, as will be described below.

With reference to FIGS. 2-5, there is shown a testing device generally designated 56 having a body member 58. The body member has a dish-shaped cavity 60 at an outer side surface 62 of the body member 58. The body member 58 has a passageway 64 communicating with a lower end of the cavity 60 at an opening 66. The body member 58 also has a tubular section 68 at a distal end 70 of the body member 58, with the tubular section 68 defining an outer end portion of the passageway 64 and an opening 72 at the distal end of the body member. As shown, the passageway 64 has a first channel 74 communicating with the cavity opening 66 and disposed generally vertically when the cavity 60 is placed in an upright position, and a second channel 76 disposed generally horizontally during testing and communicating between the channel 74 and the end opening 72. The body member 58 also has an elongated bar 78 at a proximal end 80 of the body member 58 defining a pair of opposed wings 82 which extend past opposed sides 84 of the body member 58. As shown, a central portion 86 of the body member 58 connects the tubular section 68 and the elongated bar 78. The body member 58 may be made of any suitable material, such as plastic.

The use of the device 56 for testing the needle location in the patient's body is described as follows. With reference to FIGS. 6–8, after the needle 20 and stylet 32 have been positioned in the body, as previously described, the stylet 32 is removed from the needle 20. Next, the testing device 56 is attached to the needle hub 22 by positioning the tubular section 68 of the body member 58 in the lumen 27 of the hub 22, and with the cavity 60 of the body member 58 located in an upright position. With reference to FIG. 7, a small quantity of testing liquid, such as a saline or anesthetic solution, is then placed by a syringe in the cavity 60 of the body member 58. Referring to FIG. 8, the physician grasps the opposed wings of the bar 78 and advances the needle 20 and attached body member 58 slightly into the patient's body. When the needle tip 28 is located in the epidural space e of the patient, the needle tip communicates with the slight negative pressure in the epidural space e, causing the testing liquid L to be drawn from the cavity 60 into the passageway 64 of the body member 58 and the lumen 27 of the needle 20. Thus, loss of the testing liquid L from the cavity 60 into the body member 58 provides an indication that the needle tip 28 is properly located in the epidural space e of the patient.

However, with reference to FIG. 9, if the needle tip 28 has been inadvertently passed through the dura mater d into the subarachnoid space s, the needle tip 28 communicates with the positive pressure in the subarachnoid space s, causing the testing liquid L to pass outwardly from the cavity 60 around the body member 58. Accordingly, the testing device 56 also indicates whether the needle tip has improperly punctured the dura mater d, in which case the needle 20 must be withdrawn a slight distance from the patient. The testing liquid L may be again placed in the cavity 60 for determining when the needle tip 28 is located in the epidural space e. After the needle has been properly positioned in the patient with the needle tip 28 located in the epidural space e, the testing device 56 is removed from the needle hub 22, and the epidural anesthesia procedure proceeds in the normal manner.

Thus, in accordance with the present invention the testing device permits easy attachment and removal of the body member 58 from the needle hub 22, and provides a sure indication when the needle tip has been properly positioned in the epidural space e of the patient. The testing device 56 also indicates whether the needle tip 28 has been improperly positioned in the subarachnoid space s of the patient. Alternatively, during certain procedures it is necessary to position the needle tip in the subarachnoid space, and the device of the present invention may be used to indicate when the needle tip has punctured the dura mater and is properly located in the body.

According to a method of the present invention, the position of a needle assembly is tested by positioning a tip of the assembly inside the patient's body, by placing a testing liquid in an upright cavity of the assembly, and by advancing the assembly into the body while determining the body pressure adjacent the needle tip with the testing liquid.

The foregoing detailed description is given for clearness of understanding only, and no unnecessary limitations should be understood therefrom, as modifications will be obvious to those skilled in the art.

I claim:

1. A method of testing the position of a needle assembly in the epidural space of a patient's body, the assembly having a tip and an elongated passageway communicating between the tip and a shallow open cavity, comprising the steps of:

positioning the tip and a distal passageway portion of the assembly inside the patient's body with the tip located adjacent the epidural space and with the cavity located outside the patient's body in an upright position;

placing a testing liquid in the upright cavity of the assembly; and advancing the assembly into the body while determining whether the testing liquid passes from the cavity to the passageway or the exterior of the needle assembly to ascertain the position of the needle assembly tip in the patient's body.

2. The method of claim 1 including the step of withdrawing the assembly slightly from the patient's body and repeating the placing and advancing steps if the testing liquid passes from the cavity to the exterior of the needle assembly.

3. The method of claim 1 including the step of stopping advancement of the assembly if the testing liquid passes from the cavity into the passageway.

* * * * *